United States Patent
Nasr

(10) Patent No.: US 11,141,266 B2
(45) Date of Patent: Oct. 12, 2021

(54) TRANSCATHETER VALVE PROSTHESIS

(71) Applicant: HIGHLIFE SAS, Paris (FR)

(72) Inventor: Malek Nasr, Paris (FR)

(73) Assignee: HIGHLIFE SAS, Paris (FR)

( * ) Notice: Subject to any disclaimer, the term of this patent is extended or adjusted under 35 U.S.C. 154(b) by 178 days.

(21) Appl. No.: 16/575,623

(22) Filed: Sep. 19, 2019

(65) Prior Publication Data

US 2020/0008940 A1 Jan. 9, 2020

Related U.S. Application Data

(63) Continuation of application No. 15/343,936, filed on Nov. 4, 2016, now Pat. No. 10,456,247.

(51) Int. Cl.
*A61F 2/24* (2006.01)
*A61F 2/82* (2013.01)

(52) U.S. Cl.
CPC .......... *A61F 2/2418* (2013.01); *A61F 2/2412* (2013.01); *A61F 2/2415* (2013.01); *A61F 2/2457* (2013.01); *A61F 2002/828* (2013.01); *A61F 2220/0075* (2013.01); *A61F 2230/001* (2013.01); *A61F 2230/005* (2013.01); *A61F 2230/008* (2013.01); *A61F 2230/0054* (2013.01); *A61F 2230/0078* (2013.01); *A61F 2250/0029* (2013.01); *A61F 2250/0036* (2013.01); *A61F 2250/0039* (2013.01); *A61F 2250/0048* (2013.01)

(58) Field of Classification Search
USPC .................................................. 623/1.1–3.1
See application file for complete search history.

(56) References Cited

U.S. PATENT DOCUMENTS 6,139,575 A 10/2000 Shu et al.
6,231,598 B1 5/2001 Berry et al.
6,264,700 B1 7/2001 Kilcoyne et al.
(Continued)

FOREIGN PATENT DOCUMENTS

CN 101505686 A 8/2009
CN 102639179 A 8/2012
(Continued)

OTHER PUBLICATIONS

Oct. 3, 2017 Office Action issued in U.S. Appl. No. 15/343,302.
(Continued)

*Primary Examiner* — Yashita Sharma
(74) *Attorney, Agent, or Firm* — Oliff PLC

(57) ABSTRACT

A heart valve system, the system including a radially self-expandable tubular body and a valve. The tubular body having an inflow end and an outflow end, and the tubular body including a proximal-most end at the inflow end and a distal-most end at the outflow end. The tubular body including a plurality of arched beams at the outflow end of the tubular body such that the arched beams form the distal-most end of the tubular body. Connection points linking the inflow end of the tubular body and the arched beams, a number of connection points being equivalent to a number of the valve leaflets. Each arched beam being directly attached to an adjacent arched beam such that the arched beams are continuous along the entire circumference of the tubular body at the outflow end. The valve being coupled to the tubular body and including a plurality of valve leaflets.

18 Claims, 15 Drawing Sheets

(56) References Cited

U.S. PATENT DOCUMENTS

| | | |
|---|---|---|
| 8,728,154 B2 | 5/2014 | Alkhatib |
| 8,801,769 B2 | 8/2014 | Chobotov |
| 8,992,597 B2 | 3/2015 | Boyle et al. |
| 9,125,740 B2 | 9/2015 | Morriss et al. |
| 9,216,076 B2 | 12/2015 | Mitra et al. |
| 2002/0198594 A1 | 12/2002 | Schreck |
| 2003/0109923 A1 | 6/2003 | Chinn et al. |
| 2004/0186565 A1 | 9/2004 | Schreck |
| 2004/0236405 A1 | 11/2004 | Kula et al. |
| 2005/0085900 A1 | 4/2005 | Case et al. |
| 2007/0225796 A1 | 9/2007 | Yadin et al. |
| 2008/0275550 A1 | 11/2008 | Kheradvar et al. |
| 2009/0222076 A1 | 9/2009 | Figulla et al. |
| 2010/0168839 A1 | 7/2010 | Braido et al. |
| 2011/0112632 A1 | 5/2011 | Chau et al. |
| 2011/0208298 A1 | 8/2011 | Tuval et al. |
| 2012/0035722 A1 | 2/2012 | Tuval |
| 2012/0053682 A1 | 3/2012 | Kovalsky et al. |
| 2012/0078357 A1 | 3/2012 | Conklin |
| 2012/0123529 A1 | 5/2012 | Levi et al. |
| 2013/0184813 A1 | 7/2013 | Quadri et al. |
| 2014/0005777 A1 | 1/2014 | Anderl et al. |
| 2014/0194983 A1 | 7/2014 | Kovalsky et al. |
| 2014/0222136 A1 | 8/2014 | Geist et al. |
| 2014/0222142 A1 | 8/2014 | Kovalsky et al. |
| 2014/0277402 A1 | 9/2014 | Essinger et al. |
| 2014/0277417 A1 | 9/2014 | Schraut et al. |
| 2014/0277427 A1 | 9/2014 | Ratz et al. |
| 2014/0296966 A1 | 10/2014 | Braido et al. |
| 2014/0324160 A1 | 10/2014 | Benichou et al. |
| 2014/0350669 A1 | 11/2014 | Gillespie et al. |
| 2015/0005874 A1 | 1/2015 | Vidlund et al. |
| 2015/0081013 A1 | 3/2015 | Braido et al. |
| 2015/0094802 A1 | 4/2015 | Buchbinder et al. |
| 2015/0164636 A1 | 6/2015 | Valdez et al. |
| 2015/0257879 A1 | 9/2015 | Bortlein et al. |
| 2015/0257880 A1 | 9/2015 | Bortlein et al. |
| 2015/0257881 A1 | 9/2015 | Bortlein et al. |
| 2015/0257882 A1 | 9/2015 | Bortlein et al. |
| 2015/0335429 A1 | 11/2015 | Morriss et al. |
| 2016/0106539 A1 | 4/2016 | Buchbinder et al. |
| 2016/0151153 A1 | 6/2016 | Sandstrom et al. |
| 2016/0220365 A1 | 8/2016 | Backus et al. |
| 2017/0165054 A1 | 6/2017 | Benson et al. |

FOREIGN PATENT DOCUMENTS

| | | |
|---|---|---|
| GB | 2513195 A | 10/2014 |
| JP | 2012-528697 A | 11/2012 |
| JP | 2015-521916 A | 8/2015 |
| WO | 2010/141847 A1 | 12/2010 |
| WO | 2014/004947 A1 | 1/2014 |
| WO | 2015/128741 A2 | 9/2015 |
| WO | 2015/132667 A1 | 9/2015 |
| WO | 2015/179473 A1 | 11/2015 |

OTHER PUBLICATIONS

Oct. 4, 2017 Office Action issued in U.S. Appl. No. 15/343,359.
Jul. 26, 2019 Office Action issued in U.S. Appl. No. 15/883,460.
Jan. 10, 2018 Office Action issued in U.S. Appl. No. 15/343,792.
Feb. 23, 2018 Office Action Issued in U.S. Appl. No. 15/343,694.
Apr. 17, 2018 Office Action issued in U.S. Appl. No. 15/343,302.
Aug. 13, 2018 Office Action issued in U.S. Appl. No. 15/343,792.
Oct. 4, 2018 Office Action issued in U.S. Appl. No. 15/883,460.
Mar. 14, 2019 Office Action issued in U.S. Appl. No. 15/343,694.
Aug. 16, 2018 Office Action issued in U.S. Appl. No. 15/343,936.
Mar. 14, 2018 Office Action issued in U.S. Appl. No. 15/343,936.
Nov. 18, 2020 Office Action issued in U.S. Appl. No. 15/343,694.
May 22, 2020 Office Action Issued in U.S. Appl. No. 15/343,694.
Dec. 26, 2019 Office Action issued in U.S. Appl. No. 15/883,460.

TRANSCATHETER VALVE PROSTHESIS

This is a continuation of application Ser. No. 15/343,936 filed Nov. 4, 2016. The entire disclosure of the prior application is hereby incorporated by reference in its entirety.

BACKGROUND

Heart valve diseases affect approximately 300,000 people worldwide each year. Those diseases translate in abnormal leaflet tissue, for example, excess tissue growth, tissue degradation/rupture, or tissue hardening/calcifying. Those diseases may also translate in abnormal tissue position through the cardiac cycle of the heart, for example, annular dilation or ventricular reshaping. Such abnormal leaflet tissue and abnormal tissue position may lead to degradation in valve function including leakage/blood backflow (valve insufficiency) or a resistance to blood forward flow (valve stenosis).

A valve replacement procedure is a minimally invasive surgical procedure in which a patient's defective heart valve is repaired. Thus, the abnormal leaflet tissue or the abnormal tissue position may be repaired in order to restore operability of the heart valve. In a valve replacement procedure, a valve prosthesis is delivered to the patient's native heart valve without removing the patient's native heart valve. Instead, the valve prosthesis replaces the functions of the native heart valve.

SUMMARY

Various embodiments of the invention provide a heart valve system. The system may include a radially self-expandable tubular body having an inflow end and an outflow end. A valve may be coupled to the tubular body, the valve including a plurality of valve leaflets. Additionally, the tubular body may include a proximal-most end at the inflow end and a distal-most end at the outflow end, and the tubular body may include a plurality of arched beams at the outflow end of the tubular body such that the arched beams form the distal-most end of the tubular body. Connection points may link the inflow end of the tubular body and the arched beams, a number of connection points being equivalent to a number of the valve leaflets. Each arched beam may be directly attached to an adjacent arched beam such that the arched beams are continuous along the entire circumference of the tubular body at the outflow end.

Various embodiments of the invention further provide a method for implanting a heart valve in a patient. The method may include delivering from a delivery catheter a radially self-expandable tubular body having an inflow end and an outflow end. A valve may be coupled to the tubular body, the valve including a plurality of valve leaflets. The tubular body may include a proximal-most end at the inflow end and a distal-most end at the outflow end, and the tubular body may include a plurality of arched beams at the outflow end of the tubular body such that the arched beams form the distal-most end of the tubular body. Connection points may link the inflow end of the tubular body and the arched beams, a number of connection points being equivalent to a number of the valve leaflets. Each arched beam may be directly attached to an adjacent arched beam such that the arched beams are continuous along the entire circumference of the tubular body at the outflow end. The method may further include expanding the tubular body such that the arched beams are disposed against tissue of a connection channel of the patient between an atrial and a ventricular chamber of a heart.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION OF EMBODIMENTS

The following detailed description refers to the accompanying drawings that show, by way of illustration, specific details in which the disclosed embodiments may be practiced. Other embodiments may be utilized and structural and logical changes may be made without departing from the scope of the present disclosure. The various embodiments are not necessarily mutually exclusive, as some aspects of embodiments can be combined with one or more aspects of other embodiments to form additional embodiments.

The disclosed embodiments are directed toward a transcatheter valve prosthesis 1 for functional replacement of a patient's native heart valve in a connection channel. The patient's native heart valve may be, for example, a mitral valve or a tricuspid valve. Transcatheter valve prosthesis 1 may serve as an artificial replacement valve for the patient's native valve.

Figure 1:
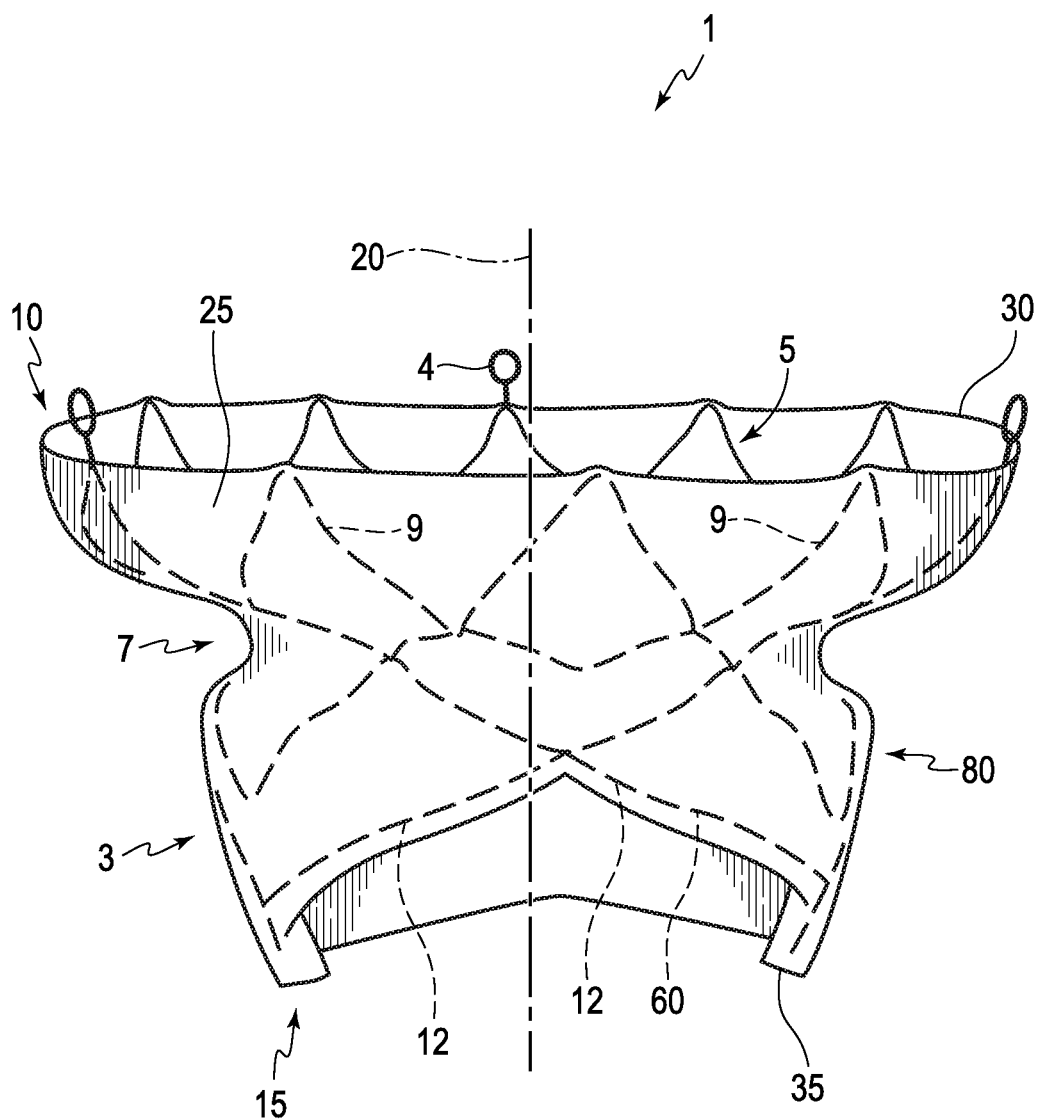
FIG. 1 schematically shows a transcatheter valve prosthesis according to embodiments.

As shown in FIG. 1, transcatheter valve prosthesis 1 includes a radially, self-expandable tubular body 5 having an inflow end 10 and an outflow end 15 (according to the direction of blood flow when the system is implanted in a patient) extending along longitudinal axis 20. In some embodiments, tubular body 5 may be balloon expandable. Tubular body 5 may include a circumferential portion 3, formed of a mesh-like structure, which is delivered within a patient via a delivery catheter. The mesh-like structure of tubular body 5 may include a plurality of struts 9 formed of a superalloy and/or a shape memory alloy including nickel, titanium, and/or precious metals (e.g., gold). In some embodiments, tubular body 5 is formed of Nitinol. In other embodiments, tubular body 5 is formed of polymers including polyvinyl-chloride, polystyrene, polypropylene, and/or another polymer. For example, tubular body 5 may be formed of one or more bioabsorbable polymers.

Tubular body 5 may be generally cylindrical in shape. Outflow end 15 of tubular body 5 may also include a frustoconical shape that slopes radially outward. Alternatively, outflow end 15 of tubular body 5 may be tapered inward. Furthermore, FIGS. 1-16 show various configurations of struts 9 of tubular body 5. Thus, it is within the scope of the present disclosure to further modify the structure and configuration of struts 9.

As shown in FIG. 1, one or more retaining rings 4 may be connected to circumferential portion 3 at inflow end 10 of tubular body 5. Retaining rings 4 may aid in the delivery and removal of valve prosthesis 1 within a patient.

Tubular body 5 may include an outer preformed groove 7 that is open to the radial outside of tubular body 5. Preformed groove 7 may be an indentation in the mesh-like structure of tubular body 5 that defines a channel. As shown in FIG. 1, preformed groove 7 may extend around an entire outer circumference of tubular body 5. In other embodiments, preformed groove 7 may extend less than the entire outer circumference of tubular body 5. Preformed groove 7 may be a continuous, non-interrupted groove, or may be an interrupted groove having, for example, two or more groove portions. In some embodiments, preformed groove 7 may be located at an axial distance, along axis 20, from both inflow end 10 and outflow end 15 of tubular body 5. Thus, preformed groove 7 may be axially spaced apart from proximal-most and distal-most ends of tubular body 5.

Preformed groove 7 may be delimited by projections (not shown) that protrude outward from tubular body 5. Thus, in some embodiments, tubular body 5 may include a first set of projections that are disposed above preformed groove 7, in an inflow direction, and a second set of projections that are disposed below preformed groove 7, in an outflow direction. Thus, the first and second set of projections may surround a top and bottom portion of preformed groove 7. The first and second set of projections may be directed toward each other. Additionally, the first and second set of projections may be members configured to pierce tissue such as, for example, spikes, triangular projections, barbs, etc.

A tubular fabric 25 may be disposed on an outer surface of tubular body 5 such that fabric 25 has an inflow end 30 and an outflow end 35. Fabric 25 may cover an entire outer surface of circumferential portion 3 of tubular body 5, or only a portion of the outer surface of circumferential portion 3. As shown in FIG. 1, fabric 25 may be disposed within preformed groove 7 such that fabric 25 follows the contours of preformed groove 7. Fabric 25 may be slack or tightly disposed on tubular body 5. As discussed further below, a trapping member 150 may be disposed around tubular body 5. Fabric 25 may be disposed on tubular body 25 such that it is in a slack state until trapping member 150 is disposed around tubular body 25. Thus, trapping member 150 may cause fabric 25 to be moved into preformed groove such that fabric 25 is in a tensioned state.

Fabric 25 may be formed of a polymer material including, for example, polyester fabric (e.g., DACRON® or other PTFE graft material). Additionally or alternatively, fabric 25 may formed of pericardium and/or a metal mesh material (e.g., a metal mesh formed of Nitinol). In some embodiments, fabric 25 may include one or more segments of material. For example, fabric 25 may include two, four, or six segments of material. The segments may be spaced apart, providing gaps between adjacent segments. Alternatively or in addition, some or all adjacent segments may overlap. Fabric 25 may include one layer of material or multiple layers of materials. In some embodiments, fabric 25 may include a coating or a liner.

Figure 2:
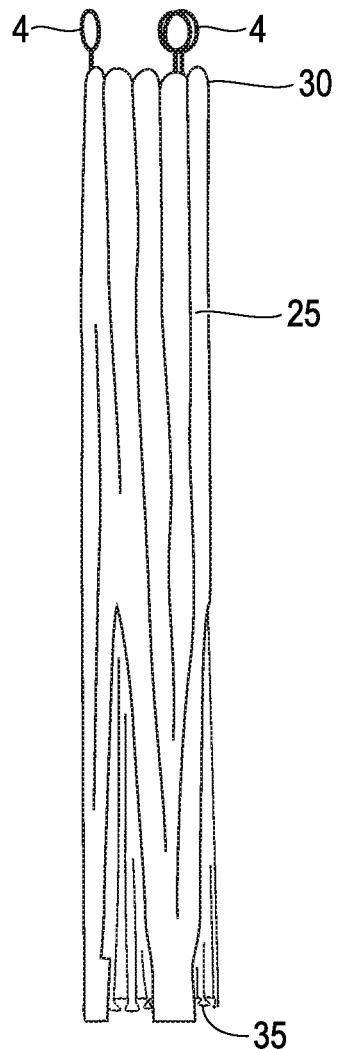
FIG. 2 schematically shows a transcatheter valve prosthesis in a contracted configuration according to embodiments.

Fabric 25 may be attached to tubular body 5 through any known securing mechanism. For example, fabric 25 and tubular body 5 may be secured through an adhesive and/or sutures. As shown in FIGS. 1 and 2, fabric 25 may be configured to assume a deployed, expanded configuration and a contracted, reduced configuration with tubular body 5. Thus, fabric 25 may be expanded and contracted based on the state of tubular body 5.

Figure 3A:
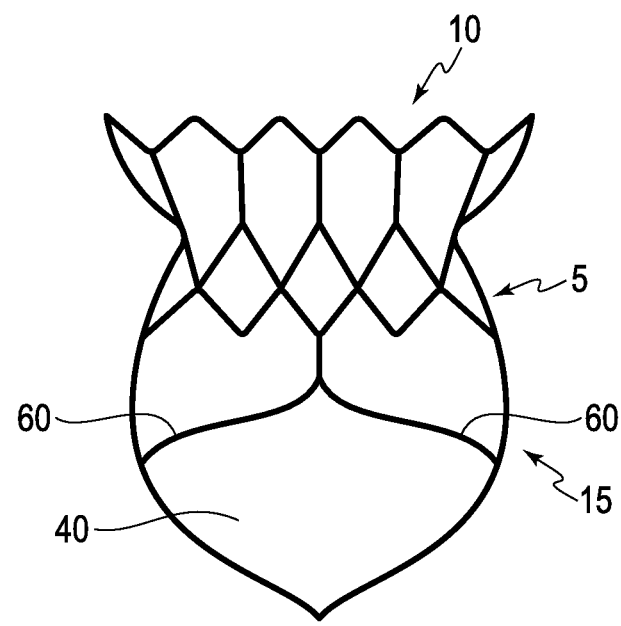
FIGS. 3A and 3B schematically show a transcatheter valve prosthesis according to embodiments.
Figure 3B:
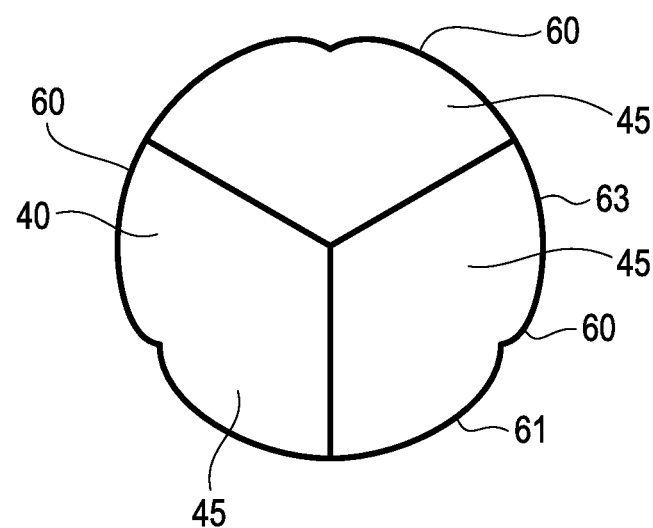

Tubular body 5 may be coupled to an artificial heart valve 40 such that at least a portion of valve 40 extends distally beyond outflow end 15 of tubular body 5 (FIG. 3A). As shown in FIG. 3B, valve 40 may include a plurality of valve leaflets 45. Valve 40 may serve as an artificial replacement for a patient's native heart valve (for example, a mitral and/or a tricuspid valve).

Figure 4A:
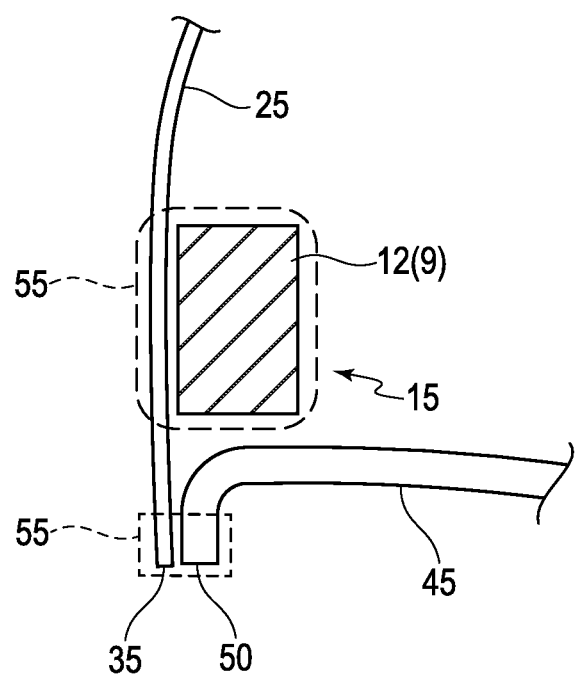
FIGS. 4A and 4B schematically show close-up views of transcatheter valve prostheses according to embodiments.
Figure 4B:
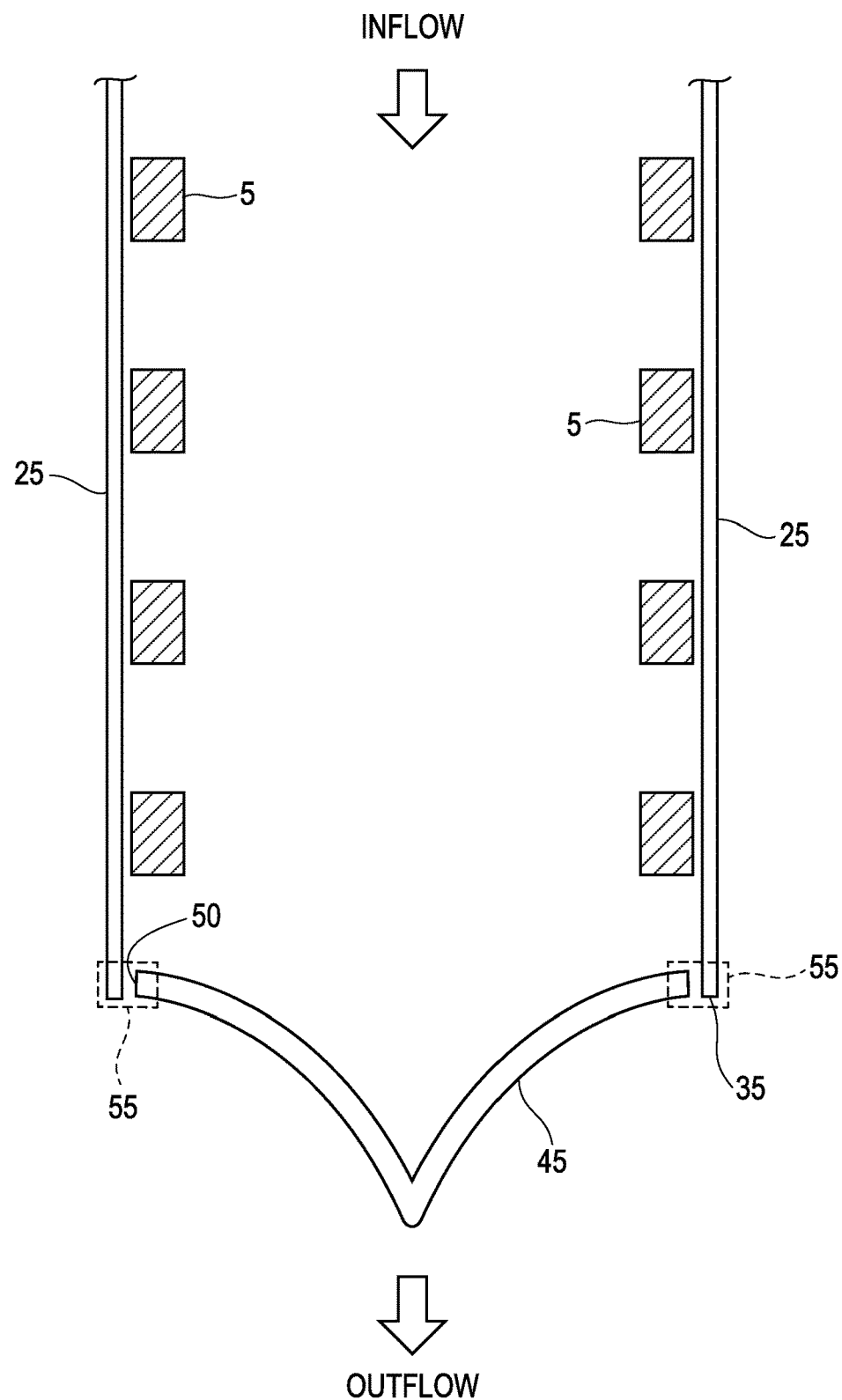

Tubular body 5 may be coupled to valve 40 such that an outer circumferential edge 50 of leaflets 45 is directly connected to outflow end 35 of fabric 25 (FIGS. 4A and 4B). Thus, as shown in FIGS. 3A, 4A, and 4B valve leaflets 45 may extend distally of outflow end 15 of tubular body 5 in an outflow direction. Valve leaflets 45 may also be distal of preformed groove 7 in an outflow direction. Outer circumferential edge 50 of leaflets 45 may axially overlap with outflow end 35 of fabric 25 such that outer circumferential edge 50 is connected to outflow end 35 with one or more sutures 55. Additionally or alternatively, outer circumferential edge 50 may be connected to outflow end 35 with any suitable securing mechanism, such as, for example, an adhesive, clips, clamps, etc.

Furthermore, tubular body 5 may be directly connected to fabric 25 such that struts 9 of tubular body 5 are connected to fabric 25 with one or more sutures 55 (FIG. 4A). Additionally or alternatively, struts 9 may be connected to fabric 25 with any suitable securing mechanism, such as, for example, an adhesive, clips, clamps, etc. Thus, as shown in FIG. 4A, valve leaflets 45 are not directly connected to tubular body 5. Therefore, valve 40 is also not directly connected to tubular body 5. Instead, valve 40 is indirectly connected to tubular body 5 through fabric 25.

As shown in FIGS. 4A and 4B, outer circumferential edge 50 of valve leaflets 45 may be disposed on an inflow side of valve 40. Thus, outer circumferential edge 50 of valve leaflets 45 may be directly connected to outflow end 35 of fabric 25 such that outer circumferential edge 50 of valve leaflets 45 axially overlaps with outflow end 35 of fabric 25 in order to provide the direct connection between valve 40 and fabric 25.

Furthermore, struts 9 of tubular body 5 that are directly connected to fabric 25 may be struts 12 located at outflow end 15 of tubular body 5 (FIGS. 1 and 4A). Struts 12 may axially overlap with fabric 25. Thus, struts 12 may provide the direct connection between tubular body 5 and fabric 25.

In some embodiments, the connection between fabric 25 and struts 12 of tubular body 5 may be located closer to inflow end 10 of tubular body 5 than the connection between fabric 25 and outer circumferential edge 50 of valve leaflets 45 (FIGS. 4A and 4B). Thus, the connection between fabric 25 and tubular body 5 may be proximal of the connection between fabric 25 and valve 40 (FIGS. 4A and 4B). It is further contemplated that the connection between fabric 25 and tubular body 5 may be located at the same axial position as the connection between fabric 25 and valve 40 such that the connections axially overlap.

Additionally, as shown in FIGS. 4A and 4B, outer circumferential edge 50 of valve leaflets 45 may be disposed distal of, in an outflow direction, of struts 12. Thus, outer circumferential edge 50 may be disposed distal of, in an outflow direction, of circumferential portion 3 of tubular body 5. Accordingly, outer circumferential edge 50 of valve leaflets 45 may not radially overlap with circumferential portion 3 of tubular body 5.

As discussed above, outer circumferential edge 50 of valve 40 is connected to outflow end 35 of fabric 25 such that valve leaflets 45 extend distally of outflow end 15 of tubular body 5 in an outflow direction (FIGS. 3A and 4B). Thus, valve 40 may not axially overlap with circumferential portion 5 of tubular body 5, and tubular body 5 advantageously has an increased compression capability. Therefore, tubular body 5 may be compressed further than conventional valve prostheses, allowing tubular body 5 to assume a smaller delivery profile.

In other alternative embodiments, valve 40 may be directly connected to outflow end 15 of tubular body 5 through one or more sutures 55. Additionally or alternatively, valve 40 may be directly connected to outflow end 15 of tubular body 5 with any suitable securing mechanism, such as, for example, an adhesive, clips, clamps, etc. In these embodiments, valve leaflets 45 may be directly connected to struts 12 such that valve leaflets 45 are connected to outflow end 15 of tubular body 5. Additionally, valve leaflets 45 may be directly connected to fabric 25 and/or fabric 25 may be directly connected to struts 12.

As shown in FIGS. 4A and 4B, outflow end 35 of fabric 25 may not extend distally, in an outflow direction, beyond outer circumferential edge 50 of leaflets 45. Thus, outflow end 35 may terminate at the location of outer circumferential edge 50. Although outflow end 35 of fabric 25 may extend distally beyond struts 12 of tubular body 5, outflow end 35 of fabric 25 does not wrap around struts 12. Thus, fabric 25 does not wrap around outflow end 15 of tubular body 5. In some embodiments, outflow end 35 of fabric 25 only wraps partially around struts 12 (and, thus, partially around outflow end 15 of tubular body 5). In these embodiments, outflow end 35 of fabric 25 does not completely wrap around struts 12. In yet other alternative embodiments, outflow end 35 of fabric 25 wraps completely around outflow end 15 of tubular body 5.

Figure 5:
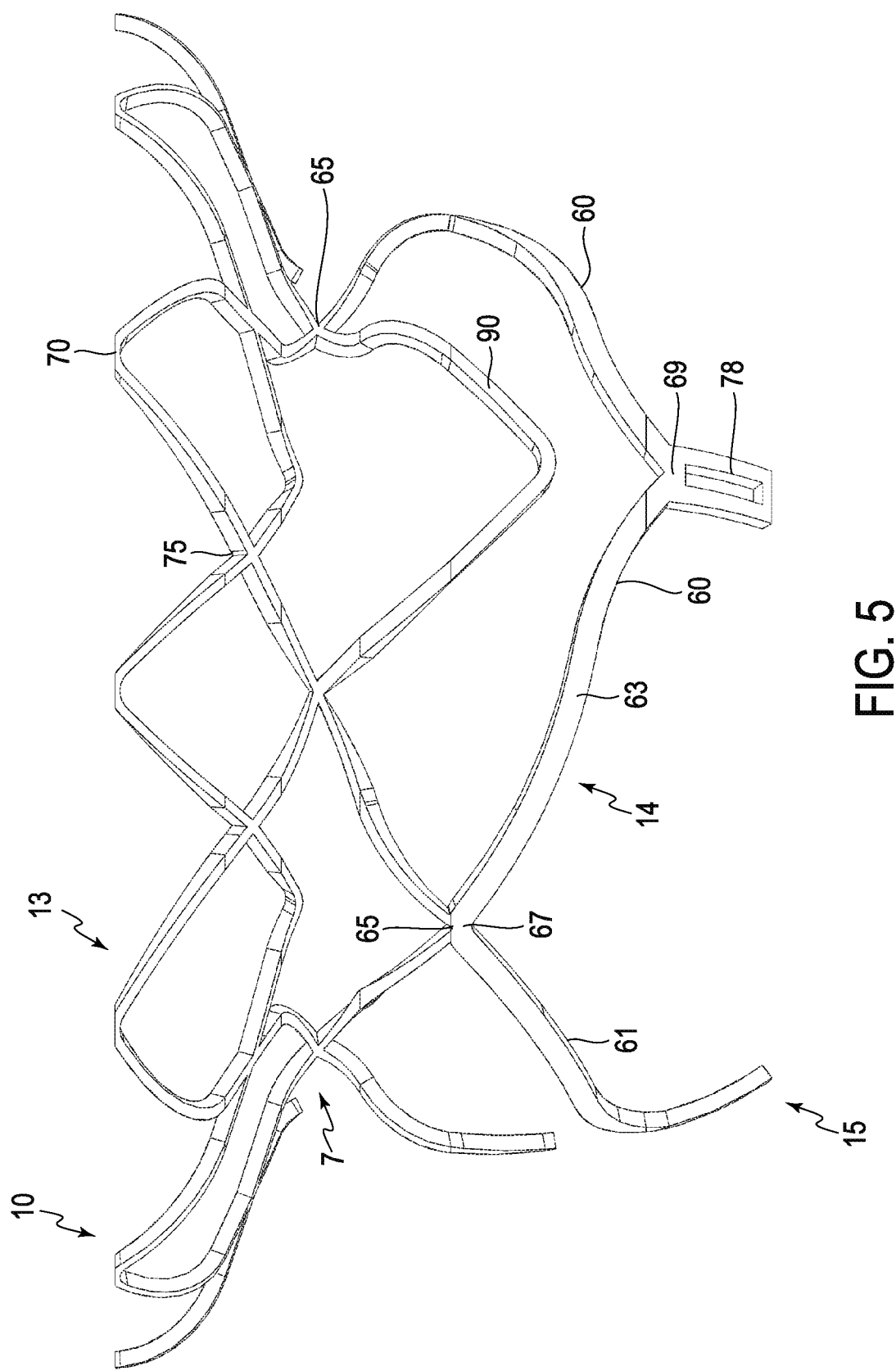
FIG. 5 schematically shows a tubular body of a transcatheter valve prosthesis according to embodiments.

As shown in FIG. 5, struts 12 of tubular body 5 may form a plurality of arched beams 60 at outflow end 15 of tubular body 5. Beams 60 may be directly connected to fabric 25, as discussed above. Thus, beams 60 may be connected to fabric 25 such that valve leaflets 45 extend distally of beams 60 in an outflow direction, as discussed above. Each beam 60 may be directly connected to an adjacent beam 60 so that the plurality of beams 60 extends around the entire circumferential length of tubular body 5 at outflow end 15. Additionally, adjacent beams 60 may be directly attached such that beams 60 are continuous along the entire circumference of tubular body 5 at outflow end 15.

Figure 6:
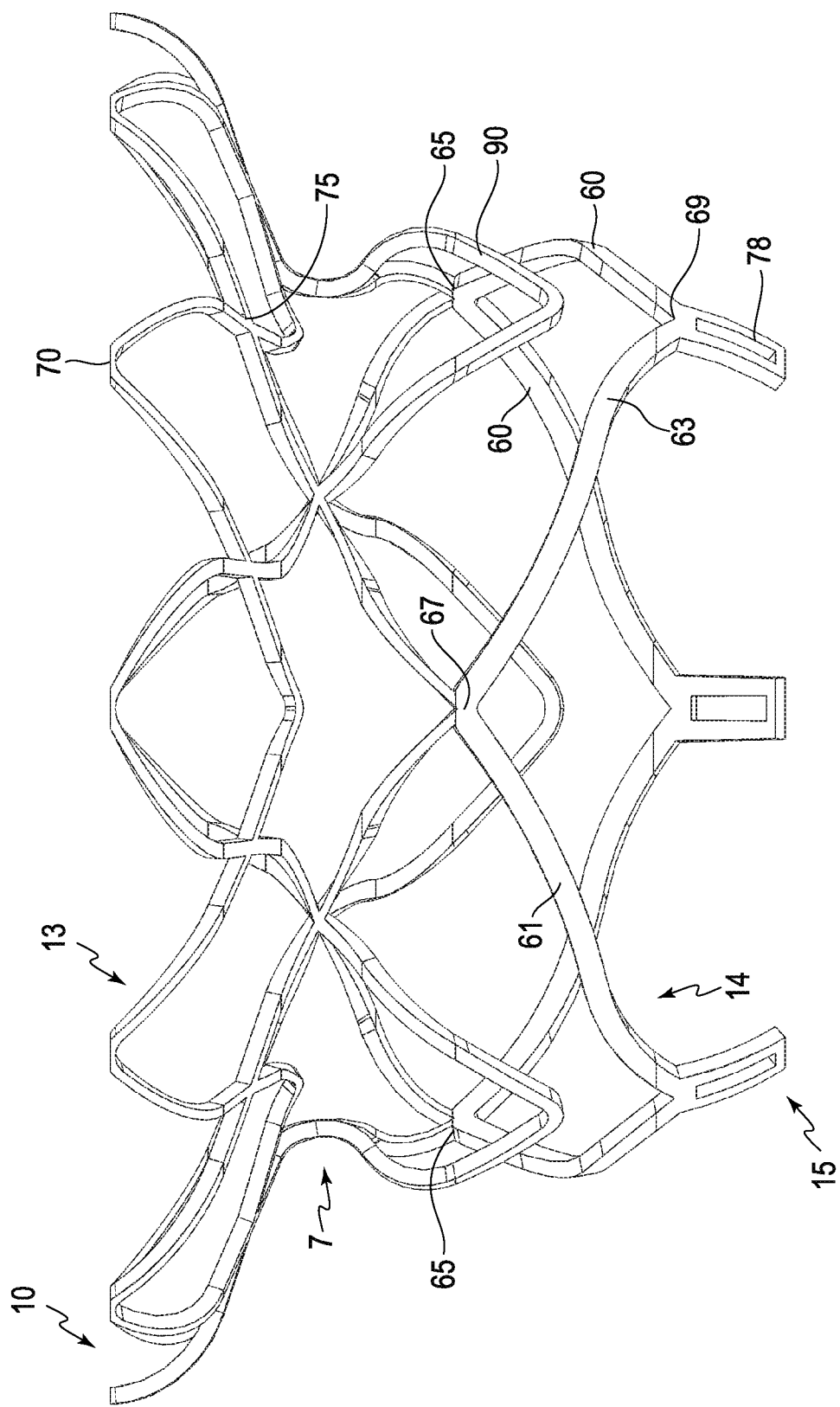
FIG. 6 schematically shows a tubular body of a transcatheter valve prosthesis according to embodiments.
Figure 7:
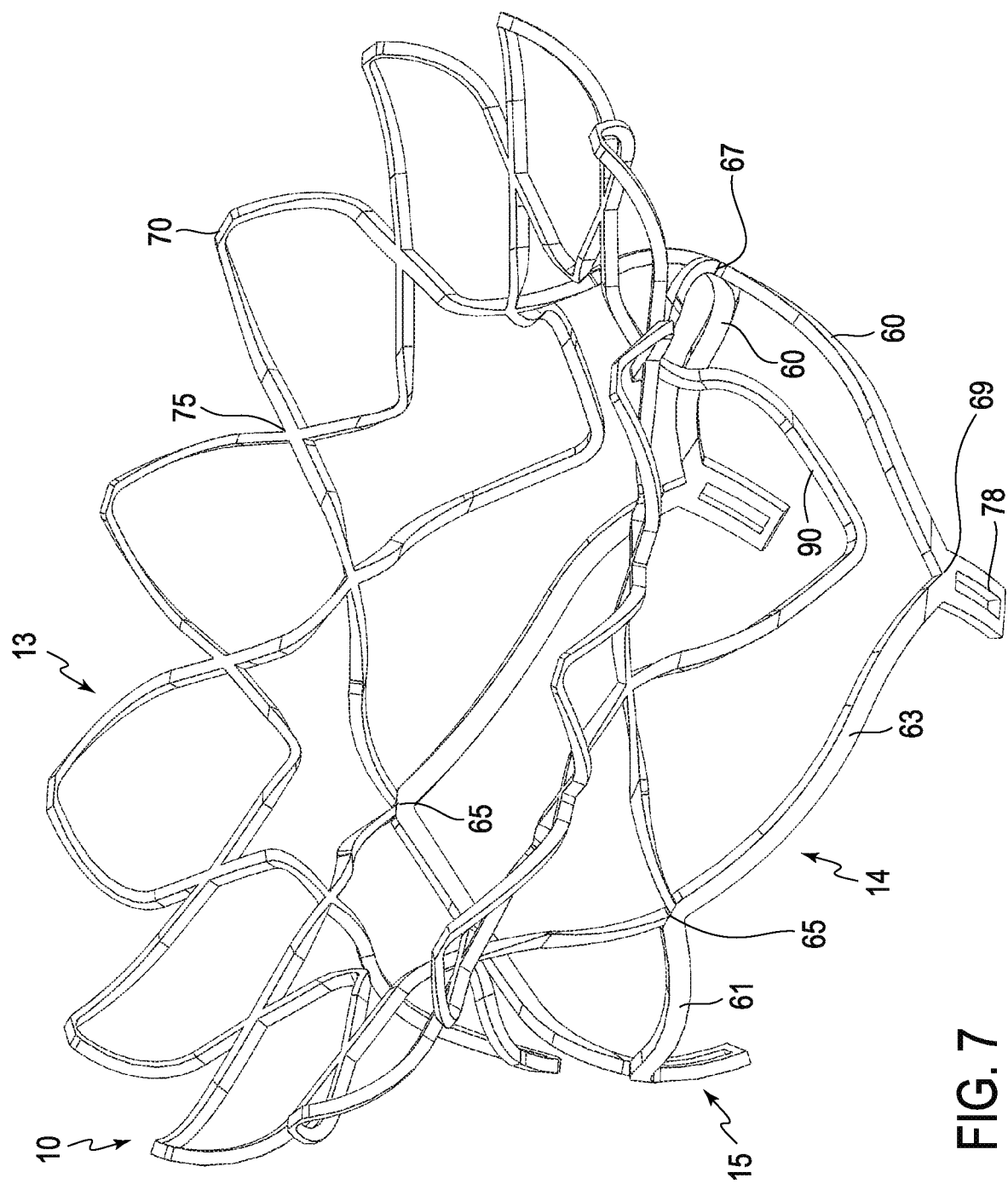
FIG. 7 schematically shows a tubular body of a transcatheter valve prosthesis according to embodiments.

Tubular body 5 may include a proximal-most end 13 at inflow end 10 and a distal-most end 14 at outflow end 15. As shown in FIGS. 5-7, arched beams 60 may form distal-most end 14 of tubular body 5. Furthermore, beams 60 may each include a first end 67 and a second end 69 such that second ends 69 are distal of first ends 67 in an outflow direction. First and second ends 67, 69 may form the arched shape of beams 60. Additionally, second ends 69 may form a commissural attachment area for attachment to valve leaflets 45.

As shown in FIGS. 5-7, for example, second ends 69 of beams 60 may be connected to one or more retaining components 78. Thus, distal-most end 14 of tubular body 5 may also be connected to retaining components 78. In some embodiments, retaining components 78 are distal of circumferential portion 3 of tubular body 5 in an outflow direction. Retaining components 78 may aid in anchoring tubular body 5 within a patient. Fabric 25 may disposed over tubular body 5 such that fabric 25 is not disposed over retaining components 78. In some embodiments, fabric 25 may not extend distally of distal-most end 14 of tubular body 5 in an outflow direction. Thus, fabric 25 may not extend distally of retaining components 78.

In some embodiments, each valve leaflet 45 may be supported by only two beams 60 of the plurality of beams 60. Thus, for example, as shown in FIGS. 3B and 5, a single valve leaflet 45 may be supported by first beam 61 and second beam 63. Each valve leaflet 45 may be supported by beams 61 and 63 such that the valve leaflet 45 is directly connected to fabric 25 that is directly connected to beams 61 and 63, as discussed above. Thus, the connections between valve leaflets 45, fabric 25, and beams 60 provide the support between beams 60 and valve leaflets 45. In other embodiments, each valve leaflet 45 may be supported by two, three, or more beams 60. Although FIGS. 5-7 show six beams, it is also contemplated that more or less beams may be used. Thus, tubular body 5 may include at least six beams 60.

As shown in FIGS. 5-7, connection points 65 may directly link inflow end 10 of tubular body 5 with beams 60. All direct links between inflow end 10 and beams 60 may be provided only by connection points 65. In the embodiments of FIG. 5-7, three connection points 65 are provided. The number of connection points 65 may be equivalent to the number of valve leaflets 45, as shown in FIG. 3B. Thus, in other embodiments, four, five or more connection points 65 may be provided, depending on the number of valve leaflets 45. In some embodiment, as shown in FIGS. 5-7, first ends 67 of beams 60 provide connection points 65.

By providing a direct link between inflow end 10 and beams 60, connection points 65 may provide a decorrelation of movement between inflow end 10 of tubular body 5 and beams 60. Thus, connection points 65 may dissociate axial and radial movements between inflow end 10 and beams 60. For example, connection points 65 may be configured to attenuate movement of inflow end 10 of tubular body 5. Thus, movement of inflow end 10 is not completely transferred to beams 60. Instead, connection points 65 may absorb movement of inflow end 10, thus providing the decorrelation effect. In some embodiments, connection points 65 absorb all movement of inflow end 10. In other embodiments, connection points 65 absorb only partial movement of inflow end 10.

As shown in FIGS. 5-7, inflow end 10 of tubular body 5 includes struts 9 with peaks 70 and valleys 75. Peaks 70 are disposed proximally of valleys 75 such that valleys 75 are located closer to outflow end 15 of tubular body 5 than peaks 70. Furthermore, peaks 70 and valleys 75 may form proximal-most end 13 of tubular body 5.

Figure 8:
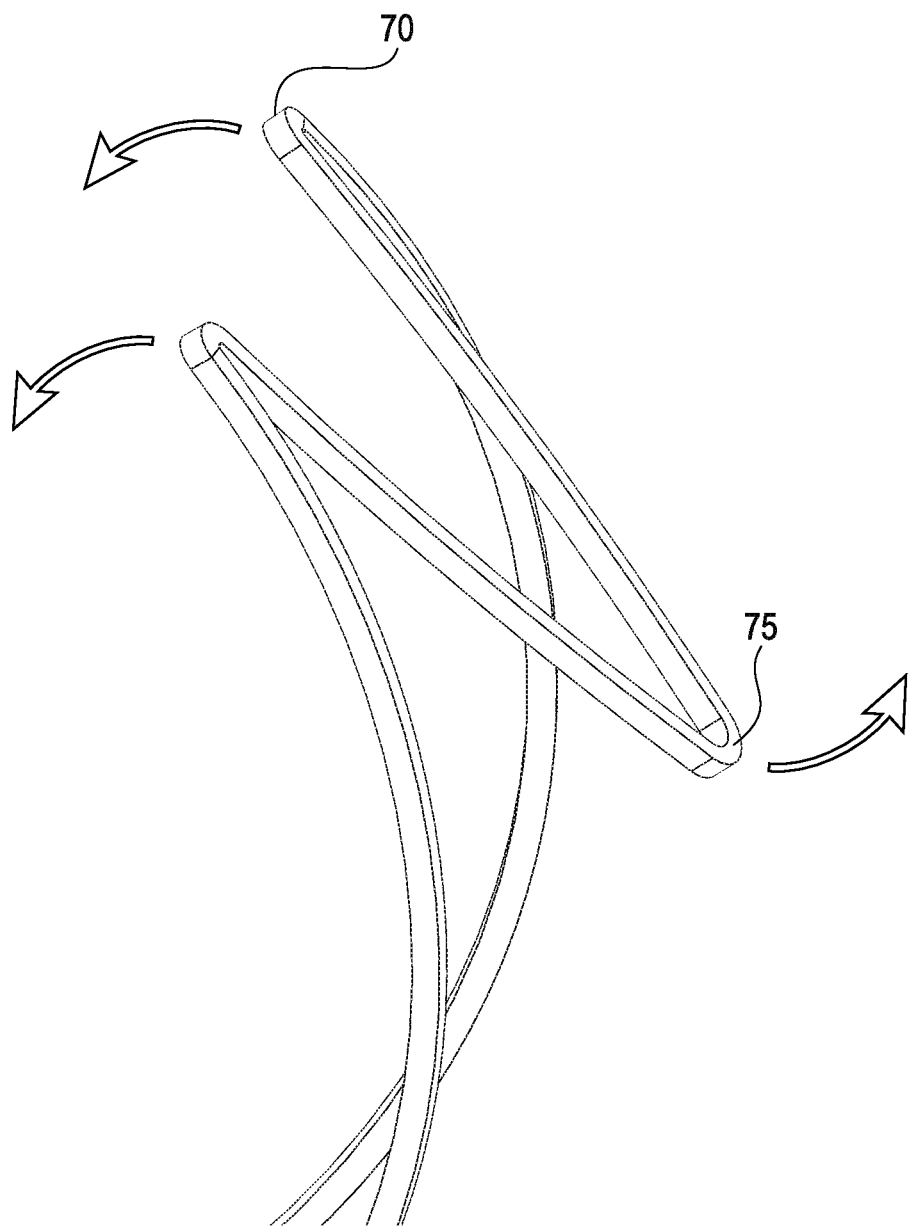
FIG. 8 schematically shows a close-up of a tubular body of a transcatheter valve prosthesis according to embodiments.

In some embodiments, peaks 70 and valleys 75 may be configured such that movement of peaks 70 radially inward may cause valleys 75 to flare radially outward (FIG. 8). For example, when tubular body 5 is implanted in a patient, the patient's atrial wall may push radially inward on peaks 70 (due to normal systolic movement of the patient's native valve). This causes peaks 70 to deform and move radially inward, as shown in FIG. 8. Accordingly, the inward movement by peaks 70 causes valleys 75 to deform and move radially outward. The deformation of valleys 75 radially outward pushes inflow end 10 further into contact with the patient's atrial wall, thus improving the sealing effect of inflow end 10 within the patient.

When fabric 25 is disposed over tubular body 5, as discussed above, movement of peaks 70 radially inward may cause both valleys 75 and fabric 25 to flare radially outward. Thus, fabric 25 is pushed further into contact with the patient's atrial wall, along with valleys 70, in order to further increase the sealing effect of tubular body 5 within the patient.

Figure 9:
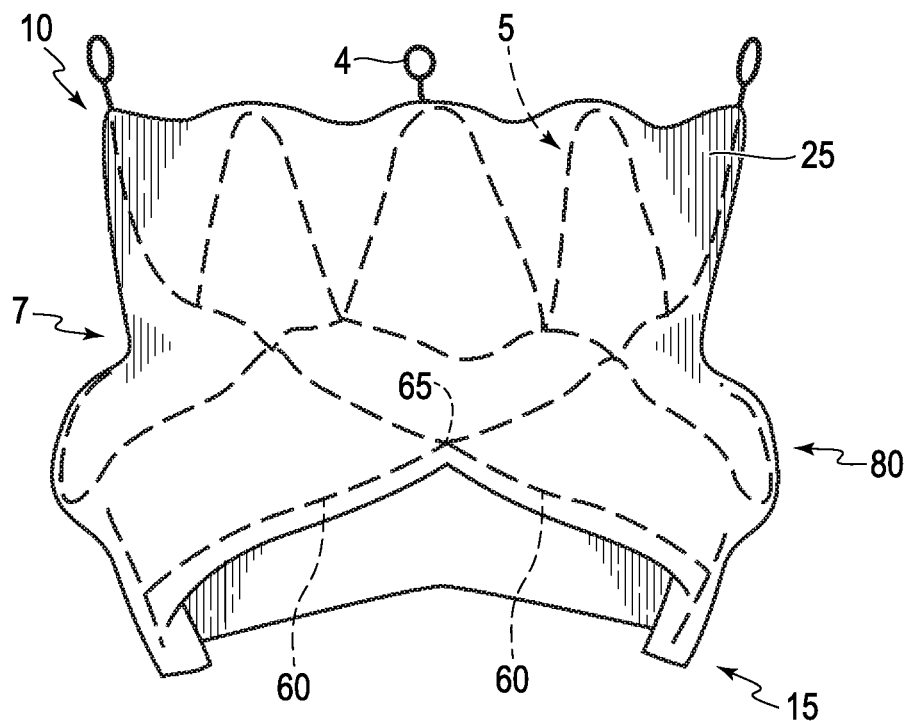
FIG. 9 schematically shows a transcatheter valve prosthesis according to embodiments.
Figure 10:
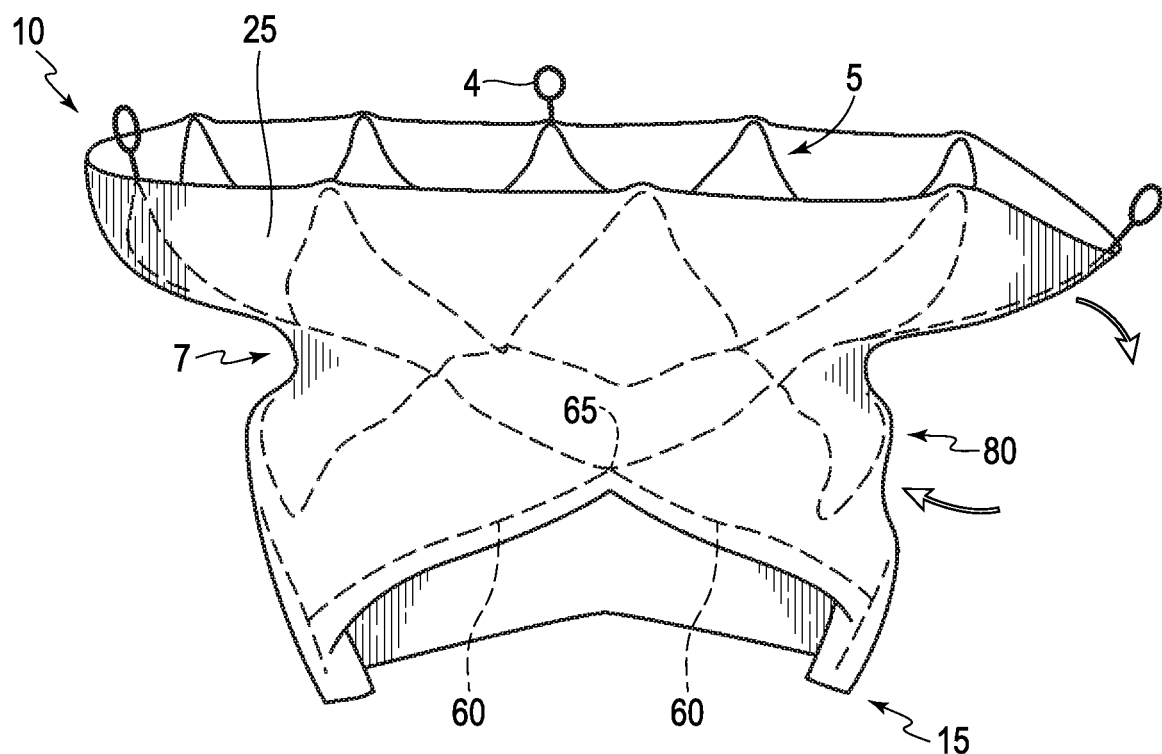
FIG. 10 schematically shows a transcatheter valve prosthesis according to embodiments.

As shown in FIGS. 1 and 9, for example, outflow end 15 of tubular body 5 may include beams 60 and a proximal section 80. Both beams 60 and proximal section 80 may be disposed distal, in an outflow direction, of preformed groove 7. Proximal section 80 may also be disposed distally of peaks 70 and valleys 75 in an outflow direction. Furthermore, beams 60 may be disposed distal, in an outflow direction, of proximal section 80. Accordingly, as shown in FIG. 10, movement of proximal section 80 radially inward may cause inflow end 10 of tubular body 5 to flare radially outward. For example, natural movement of a patient's native valve may cause an inward compression on tubular body 5. More specifically, in some examples, the patient's native valve may cause an inward compression on valve leaflets 45, which in turn may cause an inward compression on tubular body 5. Thus, such a compression may cause proximal section 80 to be compressed radially inward. Due to the structure of tubular body 5, movement of proximal section 80 radially inward causes inflow end 10 to flare radially outward. The outward movement of inflow end 10 may increase the sealing effect between inflow end 10 and a patient's atrial wall, thus advantageously providing a tighter seal between tubular body 5 and the patient's atrial wall. Furthermore, when proximal section 80 moves radially inward and inflow end 10 flares radially outward, beams 60 may not move. Thus, connection points 65 may dissociate such movement of proximal section 80 from beams 60.

As shown in FIGS. 9 and 10, connection points 65 may be disposed in proximal section 80. Alternatively, connection points 65 may be disposed distal of proximal section 80 in an outflow direction. Furthermore, in some embodiments, valve leaflets 45 may extend entirely distal of proximal section 80 in an outflow direction. In other embodiments, valve leaflets 45 may axially overlap with proximal section 80.

Figure 11:
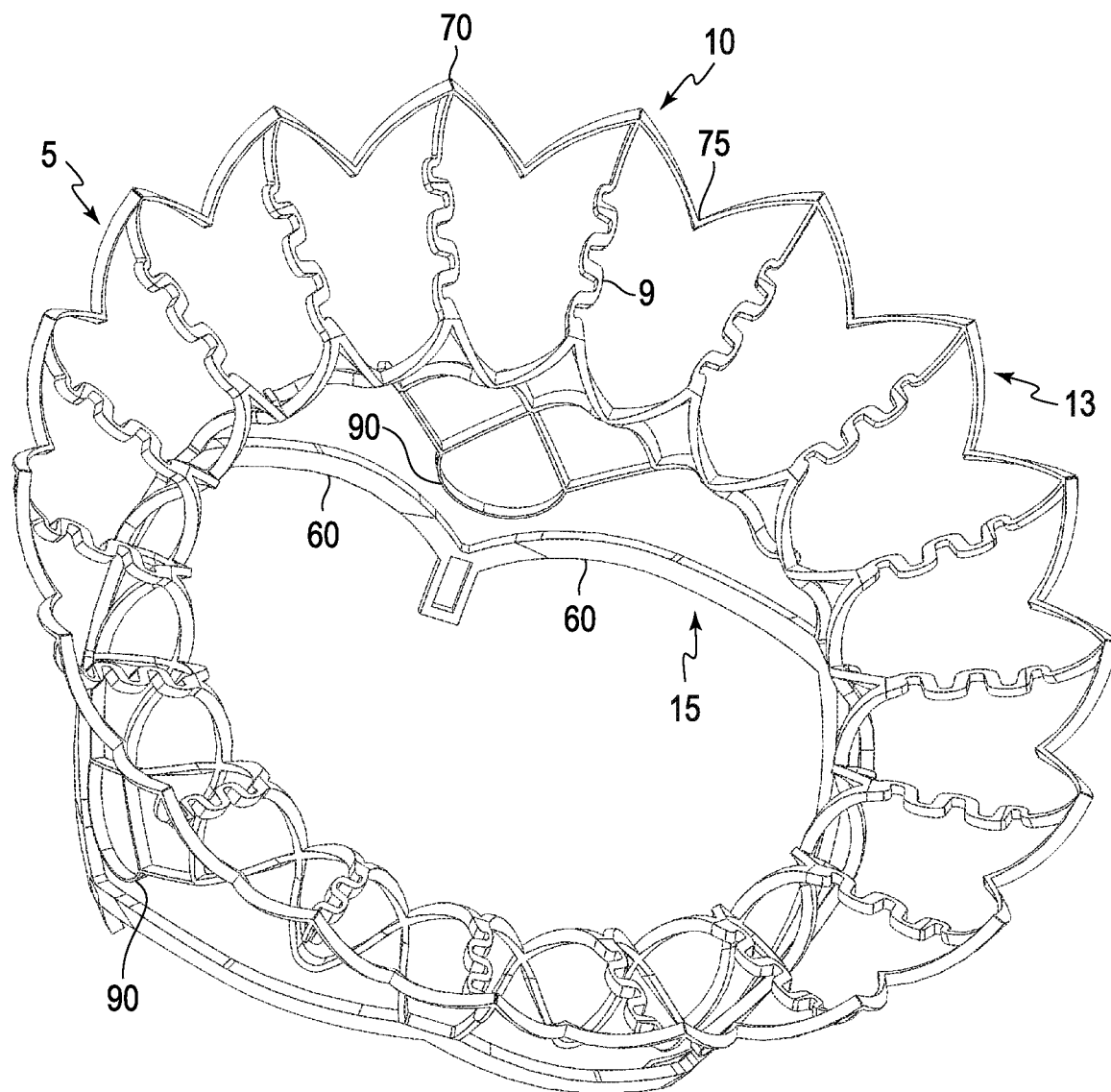
FIG. 11 schematically shows a tubular body of a transcatheter valve prosthesis according to embodiments.

FIG. 11 shows an additional configuration of struts 9 in which inflow end 10 of tubular body 5 includes struts 9 with an S-shape. The S-shaped struts may be directly connected to peaks 70 such that both peaks 70 and valleys 75 are disposed above the S-shaped struts in an inflow direction, when tubular body 5 is in an expanded state. The S-shaped struts may each form a decorrelation portion that dissociates movements between proximal-most end 13 of tubular body 6 and outflow end 15 of tubular body 5. Thus, the S-shaped struts may be configured to stress and compress in reaction to movement in inflow end 10 or outflow end 15. Thus, because the S-shaped struts stretch and/or compress, movement from one end of the tubular body 5 does not translate/communicate to the other end of the tubular body 5. The S-shaped struts may be disposed entirely proximal of preformed groove 7 in an inflow direction.

Figure 12:
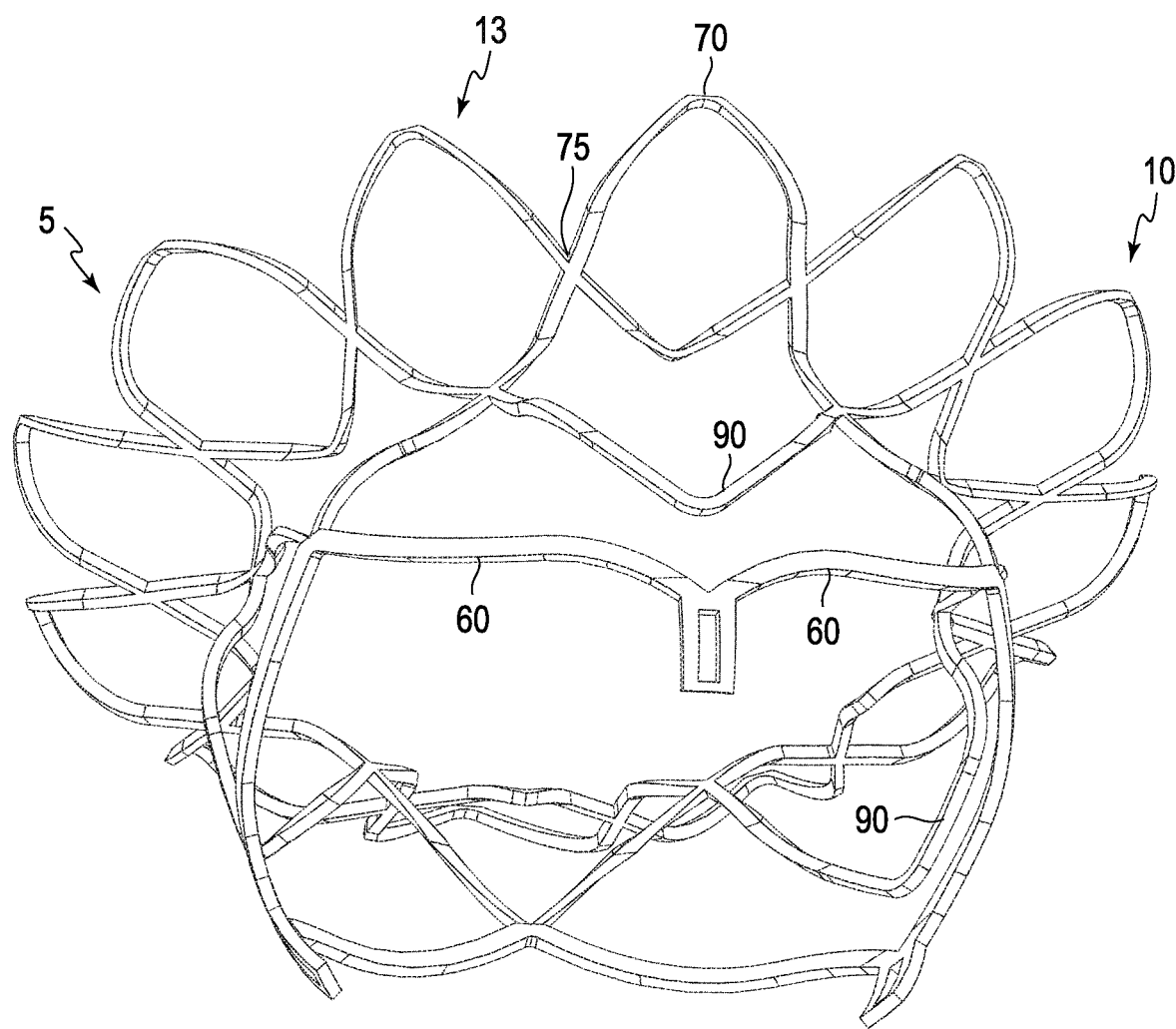
FIG. 12 schematically shows a tubular body of a transcatheter valve prosthesis according to embodiments.

In some embodiments, tubular body 5 may include a motion buffer component 90 integrated in tubular body 5 (FIGS. 11-13B). Motion buffer component 90 may include one or more struts 9 formed into, for example, a droplet shape (FIG. 11) or a triangular shape (FIG. 12). Motion buffer component 90 may be integral with the remainder of tubular body 5 such that tubular body 5 forms one unitary member. Additionally, fabric 25 may be disposed over an outer surface of motion buffer component 90.

Movement of valve leaflets 45 within a patient may cause tubular body 5 to also move within the patient. More specifically, valve leaflets 45 may move inward and outward when replacing the functions of the native valve within a patient. Such movement may cause, for example, outflow end 15 of tubular body 5 to be pushed radially inward and outward with regard to the patient's atrial wall. Such movement of outflow end 15 also causes fabric 25 to be pushed radially inward and outward with regard to the patient's atrial wall. This movement of fabric 25 against the patient's native valve may cause friction and wear on fabric 25. Furthermore, tubular body 5 may also suffer from friction and wear by continued contact with the patient's native valve.

Figure 13A:
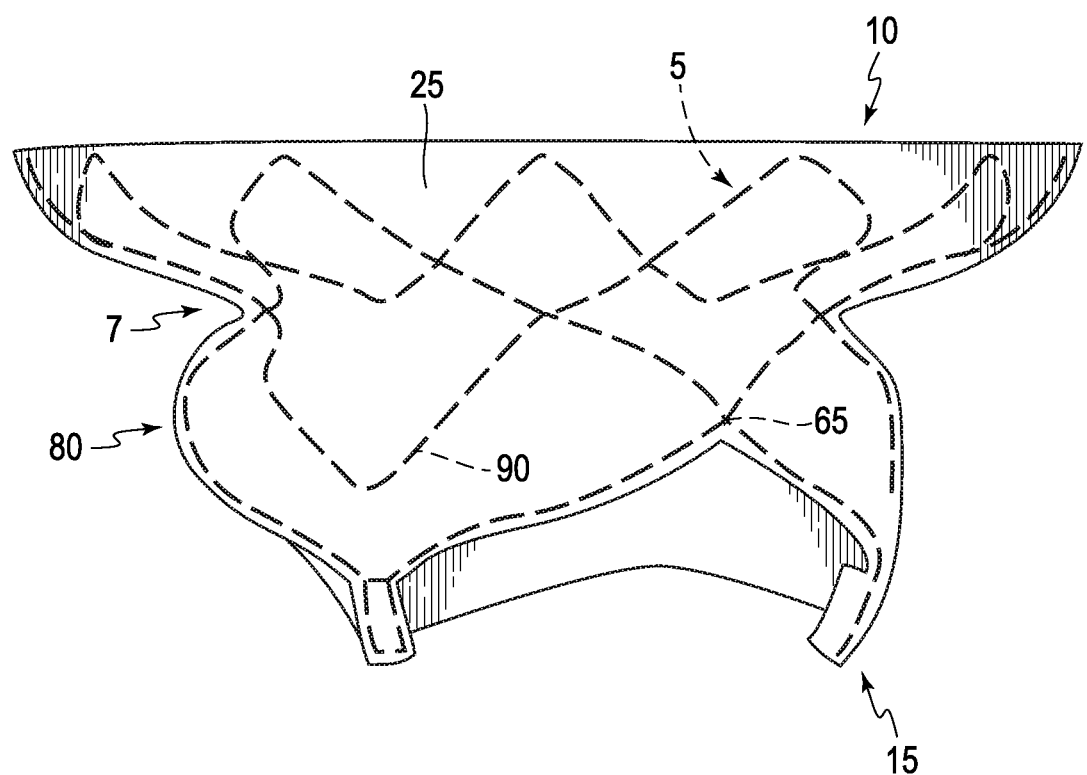
FIGS. 13A and 13B schematically show a transcatheter valve prosthesis according to embodiments.
Figure 13B:
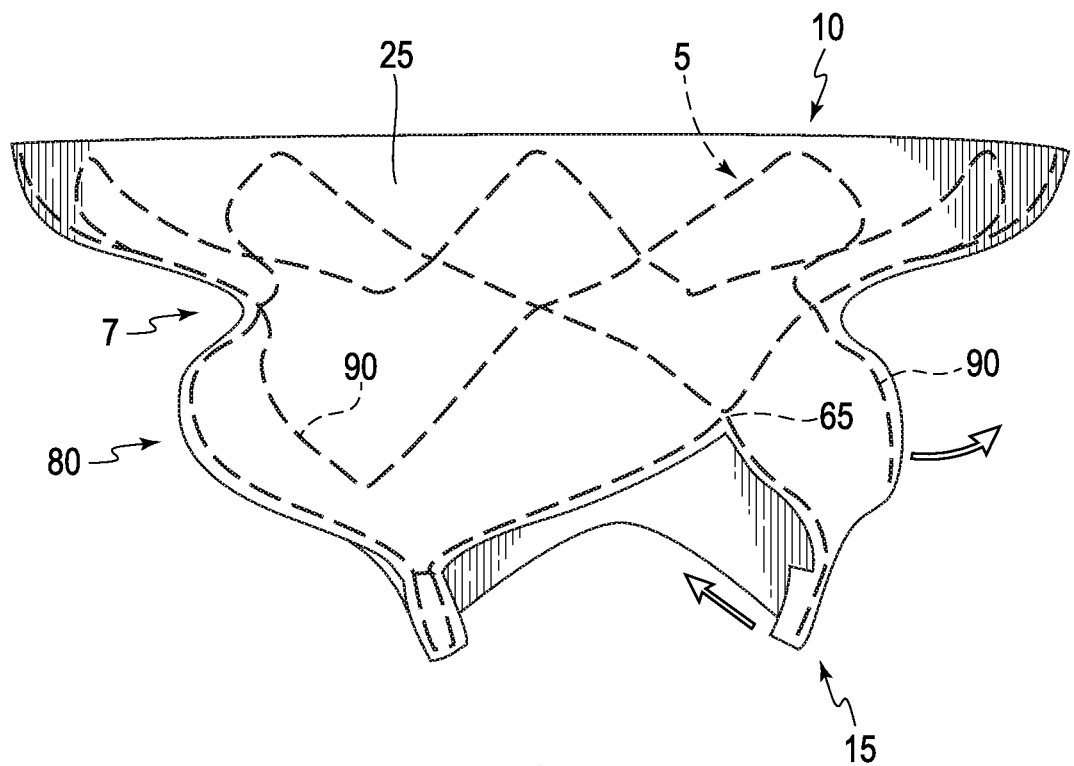

Motion buffer component 90 may create a bumper effect to reduce such friction and wear on fabric 25 and tubular body 5. For example, as shown in FIGS. 13A and 13B, when outflow end 15 of tubular body 5 moves radially inward from movement of valve leaflets 45, motion buffer component 90 may be configured to not move radially inward with outflow end 15. Instead, motion buffer component 90 may move radially outward or may stay in its position in reaction to the inward movement of outflow end 15. Thus, motion buffer component 90 may push radially outward, against fabric 25 and against the patient's native valve leaflets, when outflow end 15 moves radially inward. Such radially outward pushing by motion buffer component 90 may create the bumper effect. Thus, when outflow end 15 and fabric 25 are pushed from the radially inward position to the radially outward position (due to movement of valve leaflets 45), because motion buffer component 90 already protrudes outward, motion buffer component 90 provides a cushioning effect to soften the radially outward force of outflow end 15 and fabric 25 on the patient's native valve leaflets.

Accordingly, motion buffer component 90 may absorb friction and wear on tubular body 5 that are caused from movement of valve leaflets 45. Thus, motion buffer component 90 may advantageously make tubular body 5, especially beams 60, more durable. Additionally, motion buffer component 90 may absorb friction and wear on fabric 25 that are caused from movement of valve leaflets 45. Thus, motion buffer component 90 may also advantageously make fabric 25 more durable.

FIG. 13A shows a neutral state of tubular body 5, and FIG. 13B shows a state of tubular body 5 in which outflow end 15 is moved radially inward and motion buffer component 90 is moved radially outward. The structure and/or location of motion buffer component 90 may enable motion buffer component 90 to move radially outward or to stay in its position in response to the inward movement by outflow end 15. As shown in FIGS. 11-13B, motion buffer component 90 may be disposed adjacent to beams 60 and distal of preformed groove 7 in an outflow direction. Motion buffer component 90 may be disposed within proximal section 80. Additionally, a strut width of motion buffer component 90 may be smaller than a strut width of beams 60. Thus, motion buffer component 90 may have sufficient flexibility to move radially outward or to stay in its position, as discussed above.

In some embodiments, motion buffer component 90 may be located at the same cross-section as valve leaflets 45 in a radial direction. Thus, motion buffer component 90 and valve leaflets 45 may overlap axially along longitudinal axis 20. Additionally, motion buffer component 90 may be located at least in part at the same cross-section as connection points 65 in a radial direction. Thus, motion buffer component 90 and connection points 65 may overlap axially along longitudinal axis 20.

Figure 14:
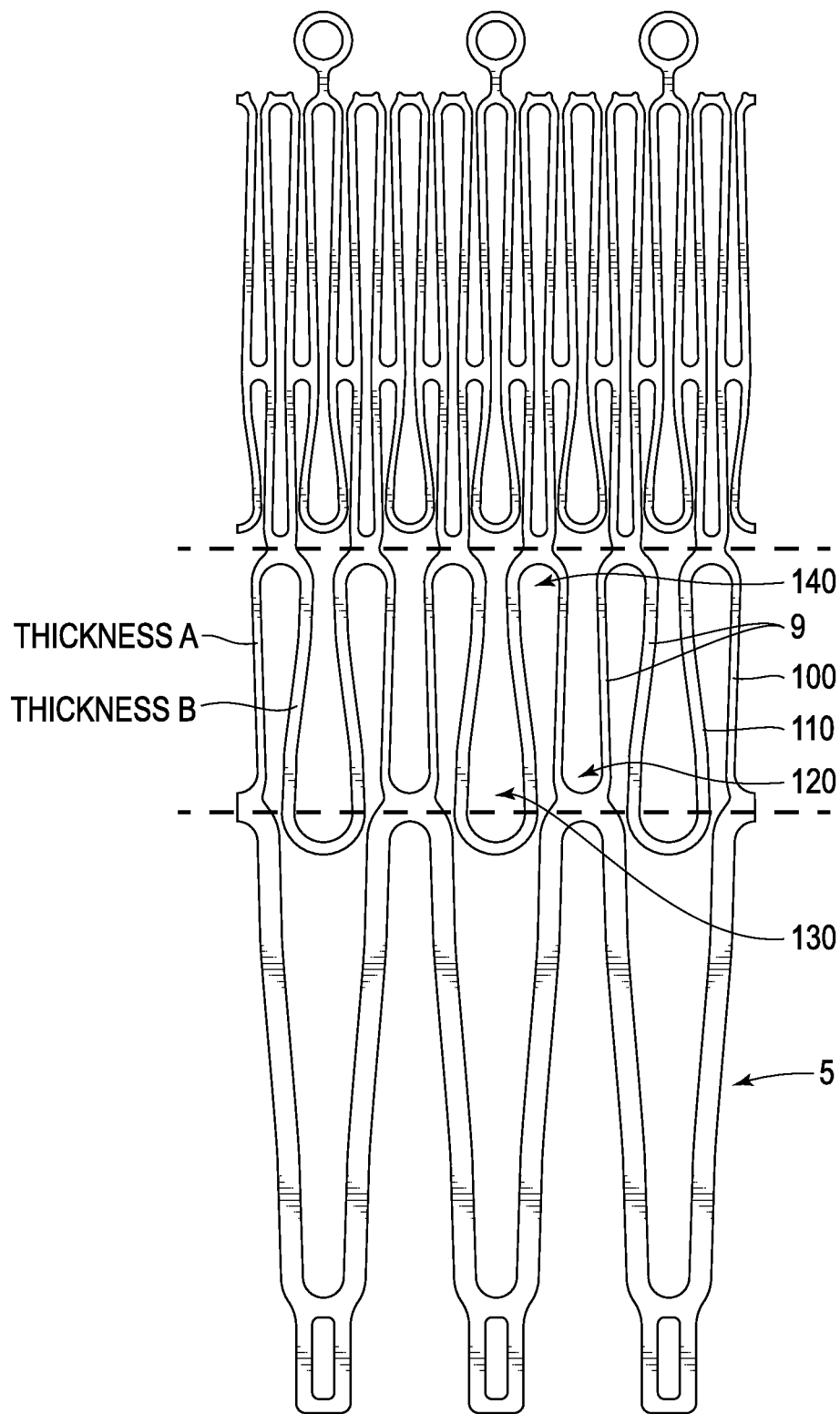
FIG. 14 schematically shows a close-up of a tubular body of a transcatheter valve prosthesis according to embodiments.

FIG. 14 shows an embodiment in which tubular body 5 includes struts 9 with different thicknesses. Thus, for example, struts 9 may include relatively smaller thicknesses 100 and relatively larger thicknesses 110. Furthermore, struts 9 may be curved in order to form first cells 120 and second cells 130. As shown in FIG. 14, first cells 120 are formed by the struts with relatively smaller thicknesses 100 and second cells 130 are formed by the struts with the relatively larger thicknesses 110. Additionally, third cells 140 may be disposed between first cells 120 and second cells 130. Third cells may be formed by both the struts with the relatively smaller thicknesses 100 and the struts with the relatively larger thicknesses 110.

First cells 120, second cells 130, and third cells 140 may be configured to open and expand uniformly when tubular body 5 is opened and expanded. Thus, the struts with relatively smaller and larger thicknesses 100, 110 allow all cells 120, 130, 140 to open together at the same rate. In contrast, in traditional prosthesis devices, some strut cells may require less outward force to open, depending on their placement in the mesh structure of the prosthesis device. Therefore, some struts cells may open easier and quicker than other strut cells. Such results in the prosthesis being expanded and opened non-uniformly. For example, the strut cells that open easier may fully open before the strut cells that are harder to open. Such non-uniform expansion may result in inaccurate placement of the prosthesis device and may alter the prosthetic valve's performance. Because cells 120, 130, 140 open together at the same rate, valve prosthesis 1 expands uniformly during manufacturing (e.g., during its heat shaping process). Accordingly, cells 120, 130, 140 provide a prosthesis device that is easier to manufacture compared to traditional prosthesis devices.

In the embodiment of FIG. 14, the struts with the relatively larger thicknesses 110 may be placed at locations on tubular body 5 that open relatively easier. The struts with the relatively smaller thicknesses 100 may be placed at locations on tubular body 5 that open with relatively more difficultly. Thus, the thickness of the struts may counter balance with the ease of opening in order to provide uniform expansion across all cells of tubular body 5.

All embodiments of valve prosthesis 1 may include positioning and/or orientation devices (not shown) to facilitate relative and/or absolute positioning of tubular body 5. These devices may include passive markers that are fixedly attached to tubular body 5. The passive markers may be made from materials different from the materials of tubular body 5 in order to improve contrast during medical imaging, e.g., using magnetic resonance or X-ray based imaging techniques. The passive markers may, for example, be made of highly radio-opaque materials thereby allowing one to precisely acquire the relative and/or absolute position of the components of valve prosthesis 1 with respect to the patient's body.

The structure of valve prosthesis 1 may allow for a smaller outer profile than conventional prosthesis. Thus, for example, valve prosthesis 1 may be sized according to human anatomies and may be compressed into a 26F ID tubing catheter for delivery within a patient. Additionally, because valve leaflets 45 extend distally beyond tubular body 5, the size of the frame of tubular body 5 required to support valve 40 may be reduced. For example, the number of struts 9 may be reduced, thus providing a more flexible structure. Additionally, the configuration of valve prosthesis 1 provides a better geometrical stability for valve leaflets 45 compared to conventional prosthesis.

Figure 15:
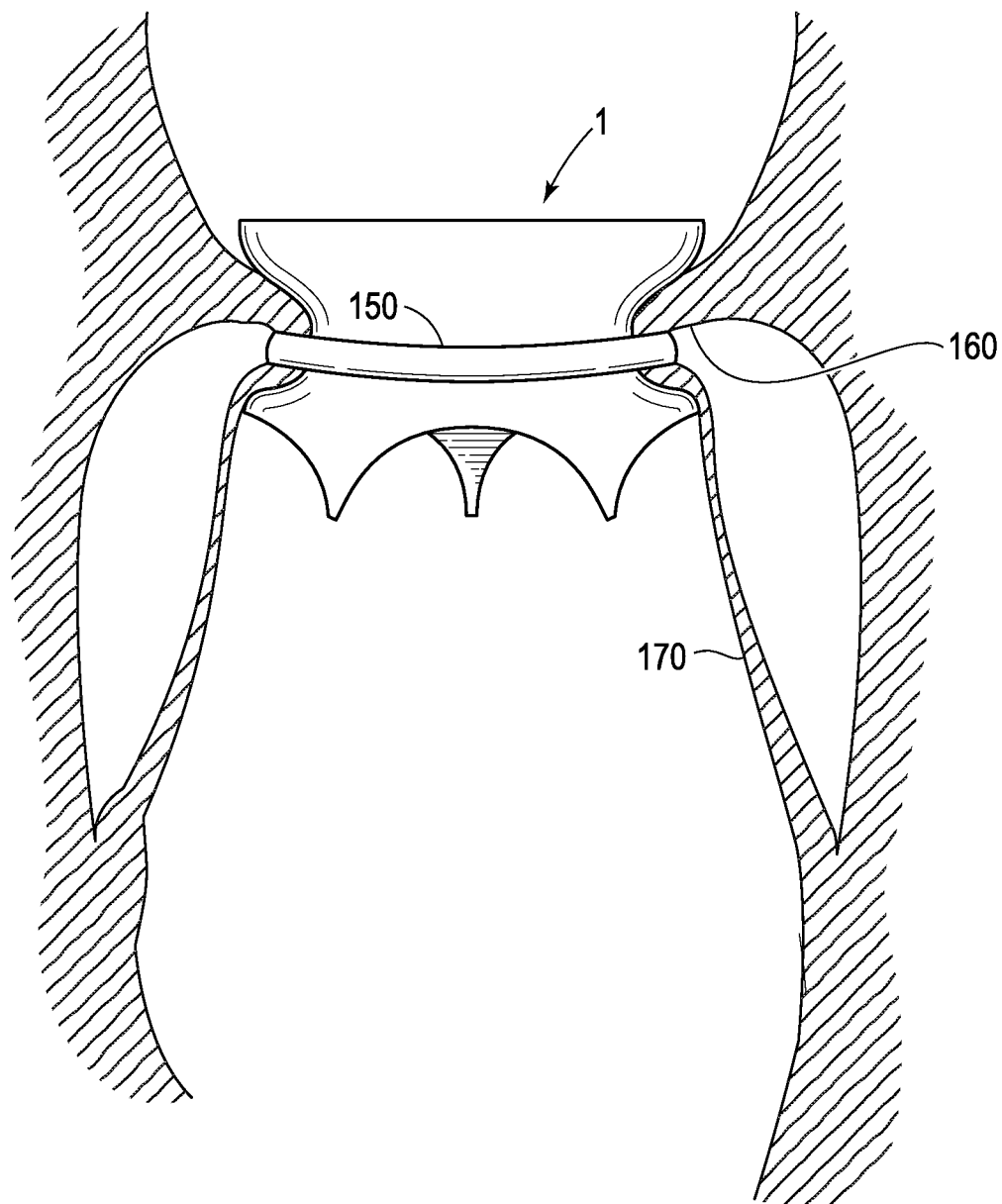
FIG. 15 schematically shows a transcatheter valve prosthesis implanted in a patient according to embodiments.
Figure 16:
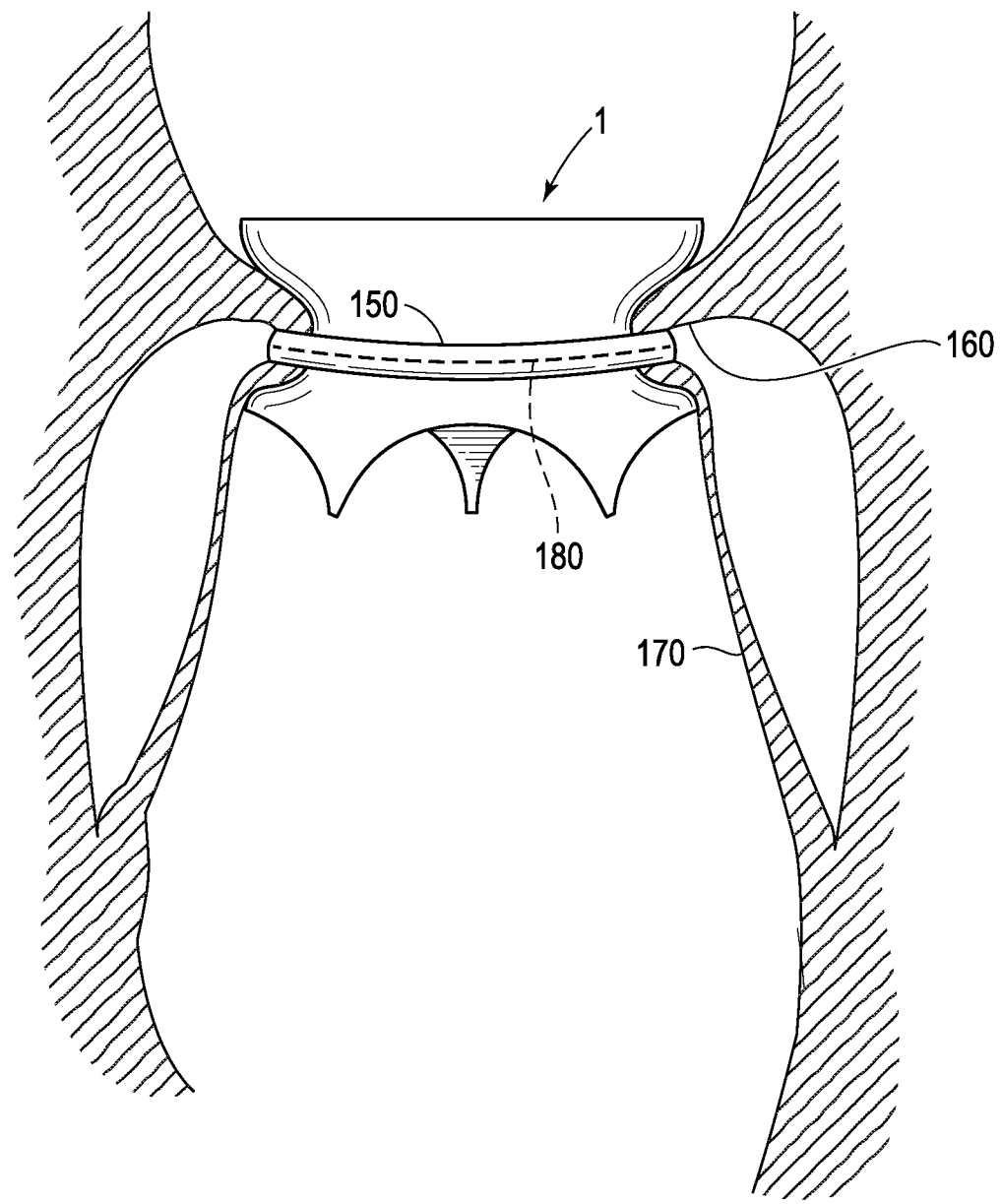
FIG. 16 schematically shows a transcatheter valve prosthesis implanted in a patient according to embodiments.

As shown in FIG. 15, valve prosthesis 1 may be deployed, via a catheter, to a patient. The method of delivering valve prosthesis 1 may include delivering, from a delivery catheter, tubular body 5 and valve 40. Next, tubular body 5 and valve 40 may be expanded such that beams 60 of tubular 5 are disposed against tissue of a patient's connection channel between an atrial and a ventricular chamber of a heart. Thus, for example, valve prosthesis 1 may be delivered to a patient's defective mitral or tricuspid valve in order to restore operability. Valve prosthesis 1 may be delivered to a patient so that the preformed groove 7 is located on the ventricular side of the annulus of the native valve (e.g., having a distance from the native valve annulus).

To place valve prosthesis 1 within the patient's heart valve, the following approaches may be applied: (1) an arterial retrograde approach entering the heart cavity over the aorta, (2) through a venous access and through a puncture through the inter atrial septum (trans-septal approach), (3) over a puncture through the apex of the heart (trans-apical approach), (4) over a puncture through the atrial wall from outside the heart, (5) arterial access (e.g., from the femoral artery through a puncture in the groin), (6) directly through the vena cava and into the right atrium (for a tricuspid valve replacement, for example), or (7) any other approach known to a skilled person.

For functional replacement of a patient's heart valve, valve prosthesis 1 may be fixed relative to the patient's connection channel wall structure such that an exterior of valve prosthesis 1 is sealed against blood flow. To achieve this, tissue of the patient's connection channel wall structure adjacent to the preformed groove 7 may be forced or placed inside preformed groove 7.

The method may further include advancing a trapping member 150 around tubular body 5 and around preformed groove 7. Thus, trapping member 150 may trap portions of native valve leaflets 160 and/or chords 170 in preformed groove 7. Such may help secure tubular body 5 in a patient. Trapping member 150 may include a full or partial loop. Additionally, trapping member 150 may be moved around tubular body 5 after tubular body 5 is fully expanded or when tubular body 5 is only partially expanded. Trapping member 150 may be loosely disposed within preformed groove such that an interference fit between trapping member 150 and preformed groove 7 secures tubular body 5 in place. Thus, trapping member 150 may serve to anchor valve prosthesis 1 within the patient. In other embodiments, trapping member 150 may exert an inward, radial force on tubular body 5 in order to anchor valve prosthesis 1 within the patient. Thus, in this embodiment, trapping member 150 may exert a frictional force on the native valve leaflets 160 and/or chords 170.

Trapping member 150 may include a delivery configuration within a delivery catheter and a deployment configuration wherein trapping member 150 is deployed from the delivery catheter. In embodiments, trapping member 150 may be biased to the deployment configuration. For example, trapping member 150 may include a shape-memory alloy such as a Nitinol or a Nitinol-based alloy.

In some embodiments, an elongate outer member 180 may also be advanced around tubular body 5 and around preformed groove 7. Elongate outer member 180 may encircle tubular body 5 after tubular body 5 is fully expanded or when tubular body 5 is only partially expanded. Elongate outer member 180 may force the patient's native valve leaflets 160 and/or chords 170 in preformed groove 7. Trapping member 150 may then be disposed over and along elongate outer member 180 in order to advance trapping member 150 around tubular body 5 and into preformed groove 7. Elongate outer member 180 may then be removed from the patient after trapping member 150 is disposed around tubular body 5. After elongate outer member 180 is removed from the patient, trapping member 150 may maintain the patient's native valve leaflets 160 and/or chords 170 in preformed groove 7.

In some embodiments, elongate outer member 180 may be a guidewire. Elongate outer member 180 may have a diameter smaller than a diameter of trapping member 150.

The disclosed methods of using valve prosthesis 1 may result in fixation of tubular body 5 in the patient's connection channel wall structure with minimal occlusion of the patient's native valve.

The disclosed embodiments also include a method for manufacturing valve prosthesis 1. The method for manufacturing may include directly connecting outer circumferential edge 50 of valve 40 with outflow end 35 of fabric 25 to form a sub-assembly. Next, tubular body 5 may be slid into the sub-assembly. Then, tubular body 5 may be connected to the sub-assembly to form an assembly such that valve leaflets 45 extend distally of outflow end 15 of tubular body 5 in an outflow direction. Tubular body 5 may be directly connected to the sub-assembly by connecting outflow end 15 of tubular body 5 with fabric 25. As shown in FIGS. 4A and 4B, fabric 25 may be directly connected to outer circumferential edge 50 and directly connected to tubular body 5 with one or more sutures 55.

What is claimed is:

1. A heart valve system, the system comprising:
a radially self-expandable tubular body having a proximal, inflow end and a distal, outflow end; the tubular body including a plurality of arched beams at the outflow end of the tubular body,
a valve coupled to the tubular body, the valve including a plurality of valve leaflets; and
a fabric that is disposed over an outer surface of the tubular body and does not wrap around the outflow end of the tubular body, the fabric being directly connected to both the arched beams and an outer circumferential edge of the valve,
wherein:
connection points link the inflow end of the tubular body and the arched beams,
each of the arched beams is directly attached to an adjacent arched beam such that the arched beams are continuous along the entire circumference of the tubular body at the outflow end, and
the arched beams and the connection points form a distal-most end of the tubular body.

2. The system according to claim 1, wherein the valve leaflets extend distally of the arched beams in an outflow direction.

3. The system according to claim 1, wherein the arched beams each include a first end and a second end, the first end providing the connection points and the second end forming a commissural attachment area, the second end being distal of the first end in an outflow direction.

4. The system according to claim 1, wherein each valve leaflet is supported by at least two beams of the plurality of arched beams.

5. The system according to claim 4, wherein each valve leaflet is supported by the at least two beams such that the outer circumferential edge of the valve is connected to the at least two beams.

6. The system according to claim 1, wherein the fabric does not extend distally of the distal-most end the tubular body in an outflow direction.

7. The system according to claim 1, wherein the plurality of arched beams includes at least six beams.

8. The system according to claim 1, wherein the distal-most end of the tubular body is connected to one or more retaining components.

9. The system according to claim 1, further comprising a trapping member disposed around an outer surface of the tubular body.

10. The system according to claim 9, wherein the trapping member is configured to trap portions of native valve leaflets and/or chords between the tubular body and the trapping member.

11. A method of implanting a heart valve in a patient, the method comprising:
delivering from a delivery catheter a radially self-expandable tubular body having a proximal, inflow end and a distal, outflow end,
a valve being coupled to the tubular body, the valve including a plurality of valve leaflets,
the tubular body including a plurality of arched beams at the outflow end of the tubular body, the plurality of arched beams being linked to the inflow end of the tubular body by connection points,
each of the arched beams being directly attached to an adjacent arched beam such that the arched beams are continuous along the entire circumference of the tubular body at the outflow end;
the arched beams and the connection points forming a distal-most end of the tubular body, and
a fabric being disposed over an outer surface of the tubular body such that the fabric does not wrap around the outflow end of the tubular body, the fabric being directly connected to both the arched beams and an outer circumferential edge of the valve, and
expanding the tubular body such that the arched beams are disposed against tissue of a connection channel of the patient between an atrial and a ventricular chamber of a heart.

12. The method according to claim 11, wherein the valve leaflets extend distally of the arched beams in an outflow direction.

13. The method according to claim 12, wherein the arched beams each include a first end and a second end, the first end providing the connection points and the second end forming a commissural attachment area, the second end being distal of the first end in an outflow direction.

14. The method according to claim 11, wherein each valve leaflet is supported by at least two beams of the plurality of beams such that an outer circumferential edge of the valve is connected to the at least two beams.

15. The method according to claim 11, wherein the fabric does not extend distally of the distal-most end of the tubular body in an outflow direction.

16. The method according to claim 11, wherein the plurality of arched beams includes at least six beams.

17. The method according to claim 11, further comprising advancing a trapping member around the tubular body to trap portions of native valve leaflets and/or chords.

18. The method according to claim 17, further comprising:
   advancing an elongate outer member around the tubular body;
   advancing the trapping member over and along the elongate outer member so that the trapping member is disposed around the tubular body; and
   removing the elongate outer member from the patient.

* * * * *